United States Patent [19]

Paris et al.

[11] 4,303,658

[45] Dec. 1, 1981

[54] ANTIVIRAL PYRAZOLOPYRAZINES

[75] Inventors: Gerárd Y. Paris, Laval, Canada; Mina D. Perlin, Highland Park, Ill.; André G. Pernet, Evanston, Ill.; Nathan L. Shipkowitz, Waukegan, Ill.

[73] Assignee: Abbott Laboratories, North Chicago, Ill.

[21] Appl. No.: 148,637

[22] Filed: May 12, 1980

[51] Int. Cl.³ ............... C07D 487/04; A61K 31/495
[52] U.S. Cl. .................................... 424/250; 544/350
[58] Field of Search .................... 544/350; 424/250

[56] References Cited

U.S. PATENT DOCUMENTS 3,957,782  5/1976  Hoehn .............................. 544/350

Primary Examiner—Mark L. Berch
Attorney, Agent, or Firm—Robert L. Niblack; Paul D. Burgauer

[57] ABSTRACT

Certain 1-substituted-3-loweralkyl-5-(substituted)phenyl-6-aminopyrazolo[3,4-b]pyrazines are provided. They have useful activity as antivirals.

12 Claims, No Drawings

ANTIVIRAL PYRAZOLOPYRAZINES

DETAILED DESCRIPTION OF THE INVENTION

Compounds of the formula

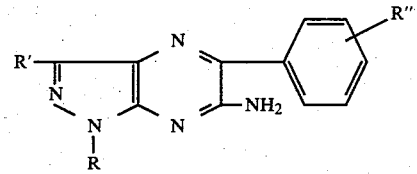

wherein R is loweralkyl, R' is hydrogen or loweralkyl and R" is hydrogen, loweralkyl, loweralkoxy, halogen or nitro exhibit useful antiviral activity against viral infections caused by rhinovirus, influenza virus and/or vaccinia virus. These compounds are of particular value because their effective dose is considerably above the dose level where toxicity is manifested in the host. The new compounds can be administered intravenously, intramuscularly or preferably, by the oral route.

The compounds of the present invention can easily be made by condensing the correspondingly 1,3-di-substituted-4-nitroso-5-aminopyrazoles with benzylcyanide wherein the phenyl ring carries the desired substituent.

In order to illustrate the manufacture and use of the compounds of the present invention, reference is made to the following examples which, however, are not meant to limit the invention in any way.

EXAMPLE 1

To a stirred solution of 0.8 g. of sodium in 75 ml. of 2-ethoxyethanol in a $N_2$-atmosphere, 2.5 g. of 5-amino-1-methyl-4-nitrosopyrazole hydrochloride was added at 5° C. Stirring was continued for 10 minutes and then, 2.0 g. of benzylcyanide was added. The reaction mixture was heated at 110°–115° C. for two hours. The mixture was then poured into 600 ml. of cold water. The formed solid was filtered off and crystallized from benzene to yield 3.1 g. (90% of theory) of 1-methyl-5-phenyl-6-aminopyrazolo[3,4-b]pyrazine, melting at 200°–202° C.

EXAMPLE 2

A solution of 5.9 g. of 1,3-dimethyl-4nitroso-5-aminopyrazole hydrochloride in 100 ml. of 2-ethoxyethanol was treated with 1.2 g. of sodium and 6.0 g. of benzylcyanide. The reaction mixture was heated for two hours before it was evaporated. The oily residue was crystallized from methanol/water to yield 5.2 g. of 1,3-dimethyl-5-phenyl-6-aminopyrozolo[3,4-b]pyrazine, melting at 174°–175° C.

EXAMPLE 3

Using the pyrazole of Example 2 with 4-fluorobenzylcyanide in the process and work-up of Example 1, a 47% yield of 1,3-dimethyl-5-(4-fluorophenyl)-6-aminopyrazolo[3,4-b]pyrazine is obtained; m.p. 208°–210° C. (softening at 200° C.).

EXAMPLE 4

Replacing the 4-fluorobenzylcyanide in Example 3 with 3-chlorobenzylcyanide produced a yield of 70% of 1,3-dimethyl-5-(3-chlorophenyl)-6-aminopyrazolo[3,4-b]pyrazine; m.p. 224°–226° C.

EXAMPLES 5–16

The following compounds were made in the same manner as described above, showing yield, melting point (m.p.) and crystallization solvent (X solvent). In all instances, R of the above structure is methyl.

| Example | R' | R" | Yield | m.p. | X Solvent |
|---|---|---|---|---|---|
| 5 | H | p-OMe | 62% | 199–201° | benzene |
| 6 | H | p-Me | 74% | 200–202° | benzene |
| 7 | H | p-Cl | 69% | 244–6° | benzene |
| 8 | Me | o-OMe | 42% | 241–3° | benzene |
| 9 | Me | p-OMe | 43% | 196–8° | benzene |
| 10 | Me | p-$NO_2$ | 30% | 292–4° | DMF/$H_2O$ |
| 11 | Me | p-Me | 50% | 207–9° | benzene |
| 12 | Me | p-Cl | 58% | 215–17° | benzene |
| 13 | Me | p-F | 60% | 208–10° | benzene |
| 14 | Me | p-Br | 55% | 213–16.5° | benzene |

Other halo analogs of the above phenyl-1-methyl- and -1,3-dimethyl-6-aminopyrazolo[3,4-b]pyrazines are obtained in similar yields. Also, the analogs wherein R' is ethyl or butyl are made in the above fashion producing yields comparable to the above. The preferred compounds, however, are those wherein R' is methyl. Particularly useful as antiviral agents are the compounds wherein R and R' are loweralkyl and R" are halogen, particularly the p-chloro moiety.

The particular compound just referred to (see Example 12) was tested at various concentrations in the standard plaque reduction assay, using monolayers of the mammaline cells mentioned in Table I. The drug was solubilized in DMSO and then further diluted with Eagle's basal medium (BME) to a final concentration of 0.5% DMSO. Of this solution, 0.5 ml. were added to the cell monolayers together with 0.1 ml. of the virus dilution shown below. After one hour, 5 ml. of a semi-solid medium containing the drug was laid over the cell layer and the plates were incubated as shown below. Following incubation, the cells were stained and the virus induced plaques were counted. The variation of the assay are shown in Table I, the results in Table II as % inhibition.

TABLE I

| Virus | Influenza | Vaccinia | Rhino |
|---|---|---|---|
| Cells | Primary chick embroy fibroblast | VERO* PRK** | Hela**** |
| Overlay | Simpson & Hirst | BME-10% FCS*** 0.5% methocel | BME-10% FCS 0.5% aqarose |
| Temp. °C. | 37° | 37° | 32° |
| Days of Incubation | 3 | 3 | 7 |
| Stain | 0.5% crystal violet, 10 min. | .0.5% crystal violet, 10 min. | TRIS-1% agar & neutral red, 5 hrs. |

*African green monkey kidney cell line - ceropithecus aethrops;
**Primary rabbit kidney cells.
***FCS = fetal calf serum.
****Hela = Human cervix carcinoma cell line

TABLE II

| Virus Concentration | 6 | 12.5 | 25 | 50 | 200 | μg/ml. |
|---|---|---|---|---|---|---|
| Influenza | 9 | 73.0 | | 91.0 | 95.0 | % |
| Rhino, Type 2 | 52 | 59 | 79 | 85 | | % |
| Rhino, Type 13 | | | 99.9 | 99.9 | | % |
| Rhino, Type 14 | | | 99.9 | 99.9 | | % |

TABLE II-continued

| Virus Concentration | 6 | 12.5 | 25 | 50 | 200 | μg/ml. |
|---|---|---|---|---|---|---|
| Vaccinia | | | | 84 | 92 | % |

The compound of Example 12 was also tested in vivo in the mouse influenza assay: mice, in groups of 10, were anesthetized with ether and infected intranasally with influenza A virus (WSN-W) using a 1-ml. syringe and a 27-gauge hypodermic needle. Each mouse received approximately 0.05 ml. of a $10^{-4}$ dilution of the virus that had an initial potency of about $10^7$ infectuous units/ml. The mice were observed for a total of 14 days at which time all surviving animals were sacrificed and the lungs removed, weighed and examined.

The severity of the infection was evaluated by the following four criteria:
A. Mortality in %
B. Average day of death
C. Average lung lesion score of survivors
D. Average lung weight of survivors.

All animals received 200 mg./kg. of the drug orally for 10 consecutive days and the proper normal and SHAM controls were used as well as amantadine for comparison. In some groups, the drug treatment was started one day before infection, in other groups on the same day and in still other groups, the drug regimen was started only after 24 hours. Statistical analysis of the results showed that 1,3-dimethyl-5-p-chlorophenyl-6-aminopyrazolo[3,4-b]pyrazine is prophylactically effective for reduction of the mortality and morbidity of mice on a statistically significant level; the drug also showed about equal results as amantadine, whether the treatment was started on day -1, 0 or +1.

The following table shows the concentration and test results on the plaque reduction test and efficacy in mice (E) with other analogs of the above formula wherein R is methyl. The test was run twice in some instances, as shown under "1" and "2".

TABLE III

| R' | R" | Conc. μg/ml | % Reduction 1 | 2 | Efficacy in Mice |
|---|---|---|---|---|---|
| Me | p-OMe | 5 | 67 | | — |
| | | 12.5-50 | 97 | 47-61 | |
| Me | p-OMe | 50 | 97 | toxic | — |
| Me | m-Cl | 5 | 0 | | — |
| | | 12.5-200 | 97 | 80 | |
| Me | p-NO$_2$ | 5 | 99.6 | | + |
| | | 12.5-200 | 92-96 | 83-85 | |
| H | p-OMe | 50-200 | 97 | 32-91 | + |
| H | p-Cl | 12.5-200 | 97 | 89-97 | + |
| H | H | 200 | 99.9 | | — |
| H | p-Me | 50-200 | 79-82 | 91 | — |
| Me | p-F | 12.5 | 63 | | + |
| Me | p-Br | 50 | 80 | | + |

While the above tests were reported only with compounds of the above structure with alkyl being methyl, other alkyl groups with 2-4 carbons give about equal results when based on molar equivalents. Also other halophenyl derivatives show good ratio between active dose and toxicity.

The effective amount for lower animals is between 10 and 250 mg./kg. In higher warm-blooded animals, including man, the effective dose is 0.5-5 g. per day, preferably 1-3 g., administered as a single dose or in equal multiple doses to produce a daily oral administration of 0.5-5 g.

Since the compounds are orally active, solid pharmaceutical dosage forms are particularly well suited for administration to warm-blooded animals. This may be a capsule containing the named amount, or said amount may be incorporated into a tablet, pill, or wafer. Tablets and the like are easily prepared with the usual excipient such as a lubricant, starch, coloring and/or flavoring agents, etc. A common method for making tablets comprises milling about one-half of 52 g. of cornstarch with 100 g. of the above drug and 220 g. of calcium phosphate dibasic dihydrate. This blend is milled until homogeneous and passed through a 40-mesh screen. The remaining portion of the cornstarch is granulated with water, heated, mixed with the above drug blend in a hot air oven at 50° C. and sifted through a 16-mesh screen. These granules are then mixed with 16 g. of talcum powder, 4 g. of magnesium stearate and 0.8 g. of combined coloring and flavoring agents. The mixture is blended until it is homogeneous, passed through a 30-mesh screen, blended for another 15 minutes and compressed into tablets weighing about 400 mg., using a 9/32 inches standard convex punch resulting in tablets of a hardness of 7-9 with each tablet containing 200 mg. of the drug. In similar fashion, tablets weighing 1000 or 2000 mg. can be made containing 500 or 1000 mg. of the drug, respectively.

The above drug can also be administered as a syrup, elixir or other liquid dosage form whereby the diluent contains the usual stabilizers, coloring and flavoring agents, buffers and the like. In these dosage forms, the drug is preferably provided in unit dosage fashion and may be incorporated into the liquid medium in the form of granules of no more than 100μ diameter. Granules of the above type may also be combined with the usual excipients for making chewable tablets. Chewable tablets or the liquid dosage forms are often preferred for pediatric or geriatric patients. Obviously, numerous well-known pharmaceutically acceptable liquid or solid diluents or carriers may be used in conjunction with the above drug.

The new compounds are useful to combat infections in warm-blooded animals after they have been attacked by rhinovirus, influenza virus and/or vaccinia virus. Excellent prophylactic results are also observed. This is of particular use in humans where a person has been in contact with someone affected by influenza or rhinovirus, and has a medical history that indicates utmost precautions, i.e., elderly people, last trimester of a pregnancy, etc. The new compounds are particularly valuable as they combat both rhinovirus and influenza, which are often difficult to distinguish and show almost identical symptoms. Therefore, a predetermination of the particular disease is not needed prior to the administration of the above new drugs.

We claim:
1. A compound of the formula

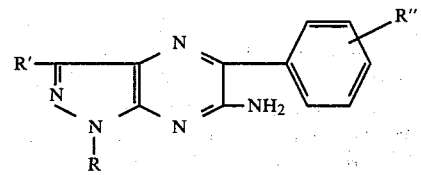

wherein R is loweralkyl, R' is hydrogen or loweralkyl, and R" is hydrogen, loweralkyl, loweralkyloxy, halogen or nitro.

2. A compound according to claim 1 wherein R and R' are methyl.

3. The compound according to claim 2 wherein R'' is chlorine in the p-position.

4. A pharmaceutical composition in dosage form containing, as the active principle, an antivirally effective amount of a compound of the formula

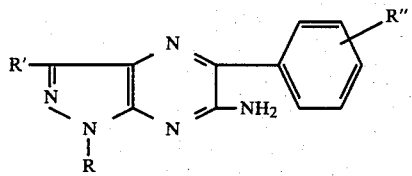

wherein R is loweralkyl, R' is hydrogen or loweralkyl, and R'' is hydrogen, loweralkyl, loweralkyloxy, halogen or nitro, together with a pharmaceutically acceptable diluent.

5. A composition according to claim 4 wherein R and R' are methyl.

6. The composition according to claim 5 wherein R'' is chlorine in the p-position.

7. The composition according to claim 4 in the form of a tablet.

8. The composition according to claim 7 wherein R and R' are methyl.

9. The composition according to claim 8 wherein R'' is chlorine in the p-position.

10. A method to combat or prevent infections in a warm-blooded animal caused by vaccinia, rhino or influenza virus, comprising administering to said animal infected by such virus, an antivirally effective amount of a compound of the formula

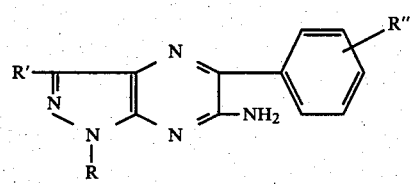

wherein R is loweralkyl, R' is hydrogen or loweralkyl, and R'' is hydrogen, loweralkyl, loweralkyloxy, halogen or nitro.

11. The method according to claim 10 wherein R and R' are methyl.

12. The method according to claim 11 wherein R'' is chlorine in the p-position.

* * * * *